United States Patent
Olmstead et al.

(10) Patent No.: US 9,934,701 B2
(45) Date of Patent: Apr. 3, 2018

(54) UNIVERSAL SPHYGMOMANOMETER SIMULATOR FOR LIVE TRAINING AND EVALUATION

(71) Applicant: Kb Port LLC, Allison Park, PA (US)

(72) Inventors: Clifford D Olmstead, Allison Park, PA (US); Charles G Miller, Allison Park, PA (US); Jerry Woods, Bellvue, PA (US); Sukhtej Dhingra, Sewickley, PA (US)

(73) Assignee: KbPort LLC, Allison Park, PA (US)

( * ) Notice: Subject to any disclaimer, the term of this patent is extended or adjusted under 35 U.S.C. 154(b) by 621 days.

(21) Appl. No.: 14/281,506

(22) Filed: May 19, 2014

(65) Prior Publication Data

US 2014/0342332 A1    Nov. 20, 2014

Related U.S. Application Data

(60) Provisional application No. 61/824,939, filed on May 17, 2013.

(51) Int. Cl.
  *G09B 23/28* (2006.01)
  *A61B 5/022* (2006.01)
(52) U.S. Cl.
  CPC ........... *G09B 23/28* (2013.01); *G09B 23/288* (2013.01); *A61B 5/022* (2013.01)
(58) Field of Classification Search
  CPC .................................................. G09B 23/28
  See application file for complete search history.

(56) References Cited

U.S. PATENT DOCUMENTS

| | | | | |
|---|---|---|---|---|
| 3,520,071 A | * | 7/1970 | Abrahamson | G06G 7/60 434/265 |
| 2005/0131465 A1 | * | 6/2005 | Freeman | A61H 31/005 607/5 |
| 2014/0182352 A1 | * | 7/2014 | Hersh | A61B 5/02141 73/1.57 |

OTHER PUBLICATIONS

Heart Beat Inc. L: Nasco Live/form Nursing Skills Training Products, Flyer #1356/RV 12-08, L:\Product\price lists\flyers\nursingskills.pdf, Dec. 2008.
Gaumard Scientific Company, Blood Pressure Training System S415 user guide, 2012.

(Continued)

*Primary Examiner* — Thomas Hong
*Assistant Examiner* — Evan Page
(74) *Attorney, Agent, or Firm* — Buchanan Ingersoll & Rooney PC

(57) ABSTRACT

A sphygmomanometer simulator for live training includes an upper arm cuff for a simulated patient; a rigid walled pressure vessel within the cuff; a manual inflator and manual release valve coupled to the rigid walled vessel to selectively increase and release the pressure within the pressure vessel; a pressure sensor coupled to the pressure vessel; a cuff controller receiving the pressure sensor measurements and controlling a speaker within the cuff to emit designated simulated Korotkoff sounds associated with a simulated blood pressure and with the pressure of the pressure vessel; a visual gauge controlled by the cuff controller and displaying a pressure associated with the pressure in the pressure vessel and simulated Korotkoff gauge bumps associated with the simulated blood pressure for the simulated patient; and a user controller coupled to the cuff controller for inputting the simulated blood pressure for the simulated patient.

21 Claims, 4 Drawing Sheets

(56) References Cited

OTHER PUBLICATIONS

Laerdal Medical, Blood Pressure Training Arm Directrions for Use. pp. 1-8, 2007.
Armstrong Medical Industries, Inc. Blood Pressure Simulator product purchase page, , https_www.armstrongmedicalcom_indexcfm_go_product, 1999-2011.

* cited by examiner

UNIVERSAL SPHYGMOMANOMETER SIMULATOR FOR LIVE TRAINING AND EVALUATION

RELATED APPLICATIONS

This application claims the benefit of U.S. Provisional Patent Application Ser. No. 61/824,939, filed May 17, 2013 entitled "Universal Sphygmomanometer Simulator For Live Training And Evaluation" which is incorporated herein by reference.

BACKGROUND INFORMATION

1. Field of the Invention

The present invention relates to a universal sphygmomanometer simulator for live training and evaluation.

2. Background Information

Sphygmomanometer

Blood pressure refers to the force exerted by circulating blood on the walls of blood vessels, and constitutes one of the principal vital signs of a patient or subject (human or animal). The pressure of the circulating blood decreases as blood moves through arteries, arterioles, capillaries and veins; the term blood pressure generally refers to arterial blood pressure, i.e., the pressure in the larger arteries, arteries being the blood vessels which take blood away from the heart. Blood pressure in humans is most commonly measured via a device called a sphygmomanometer, which traditionally uses the height of a column of mercury to reflect the circulating pressure. Although many modern blood pressure devices no longer use mercury, blood pressure values are still universally reported in millimeters of mercury.

A sphygmomanometer or blood pressure meter (also commonly referred to as a sphygmometer) is composed of an inflatable cuff to restrict blood flow, and a mercury or mechanical manometer to measure the pressure. It is always used in conjunction with a means to determine at what pressure blood flow is just starting, and at what pressure it is unimpeded. Manual sphygmomanometers are used in conjunction with a stethoscope.

The word "sphygmomanometer" comes from the Greek "sphygmós" meaning "pulse and the scientific term "manometer" meaning "pressure meter". The invention of the sphygmomanometer is commonly attributed to Samuel Siegfried Karl Ritter von Basch in 1881. Scipione Riva-Rocci is attributed with introducing a more easily used version in 1896. While in 1901, Harvey Cushing modernized the device and popularized it within the medical community.

A conventional sphygmomanometer consists of an inflatable cuff, a measuring unit (the mercury manometer, or aneroid gauge), and a mechanism for inflation which may be a manually operated bulb and valve or a pump operated electrically. The usual unit of measurement of blood pressure is millimeters of mercury (mmHg) as measured directly by a manual sphygmomanometer.

There are two categories of sphygmomanometers: manual sphygmomanometers and digital sphygmomanometers.

Manual sphygmomanometers require a stethoscope for auscultation. They are used by trained practitioners, and cannot be used in environments too noisy to permit hearing the characteristic sounds. It is possible to obtain a basic reading through palpation, but this only yields the systolic pressure. Mercury sphygmomanometers are often considered to be the gold standard for manual sphygmomanometers and measure blood pressure directly by observing the height of a column of mercury; errors of calibration cannot occur (unless the markings on the scale of millimeters are wrong). Due to their accuracy, mercury sphygmomanometers are often required in clinical trials of pharmaceuticals and for clinical evaluations of determining blood pressure for high-risk patients including pregnant women. Aneroid sphygmomanometers (mechanical types with a dial) are manual sphygmomanometers that are in common use, and can require regular calibration checks, unlike mercury manometers. Aneroid sphygmomanometers are considered safer than mercury based, although possibly less accurate. A major cause of departure from calibration is mechanical jarring. Aneroid sphygmomanometers mounted on walls or stands are less susceptible to this particular problem.

Digital sphygmomanometers typically use oscillometric measurements and electronic calculation rather than auscultation. They may use manual or automatic inflation. These are electronic, and claimed to be easy to operate without training by anybody, and can be used in noisy environments. They measure systolic and diastolic pressures by oscillometric detection, using a piezoelectric pressure sensor and electronic components including a microprocessor. They do not measure systolic and diastolic pressures directly, but calculate them from the mean pressure and empirical oscillometric parameters. Digital oscillometric monitors are also confronted with "special conditions" for which they are not designed to be used: arteriosclerosis; arrhythmia; preeclampsia; pulsus alternans; and pulsus paradoxus. The oscillometric method of detection used gives blood pressure readings that differ from those determined by auscultation, and vary subject to many factors, for example pulse pressure, heart rate and arterial stiffness. In addition to the digital oscillometric monitors drawbacks where they cannot be used, the overall accuracy of such devices has been questioned.

As a note the category of digital sphygmomanometers is defined by the method of calculating the resulting pressure rather than the type of display. A manual sphygmomanometers using auscultation may have a digital display of the associated pressure.

As shown in FIG. 1A, in humans, the cuff 16 of a typical manual sphygmomanometer 10 is normally placed by the medical professional smoothly and snugly around an upper arm 12 of a patient 14, at roughly the same vertical height as the heart while the patient is seated with the arm 12 supported. It is essential that the correct size of cuff 16, typically adjustable within a given range, is selected for the patient 14. Too small a cuff 16 results in too high a pressure, while too large a cuff 16 results in too low a pressure. For clinical measurements it is usual to measure and record blood pressure measurements of both arms of the patient 14 in the same consultation to determine if the pressure is significantly higher in one arm than the other. The cuff 16 is inflated, such as via bulb 22, until the artery 18 is completely occluded.

With the cuff 16 inflated until the artery 18 is completely occluded, a stethoscope 20 is placed in a position to listen to sounds (Korotkoff sounds) through the brachial artery 18, then medical professional slowly releases the pressure in the cuff 16 via releasing manual valve 24. As the pressure in the cuffs 16 falls, a "whooshing" or pounding sound is heard when blood flow first starts again in the artery 18. The pressure, shown on display or gauge 28, at which this sound began is noted and recorded as the systolic blood pressure 26. The cuff 16 pressure is further released until the sound can no longer be heard. The pressure reading on display 28 when the sound can no longer be heard is recorded as the diastolic blood pressure 30. In noisy environments where auscultation is impossible (such as the scenes often encountered in emergency medicine), systolic blood pressure 26 alone may be read by releasing the pressure until a radial pulse is palpated.

The sounds that medical professionals listen for when they are taking blood pressure using a manual sphygmomanometer are known as Korotkoff sounds and are named after Dr. Nikolai Korotkoff, a Russian physician who described them in 1905, when he was working at the Imperial Medical Academy in St. Petersburg.

If a stethoscope 20 is placed over the brachial artery 18 in a normal person (without arterial disease), no sound should be audible. As the heartbeats, these pulses are transmitted smoothly via laminar (non-turbulent) blood flow throughout the arteries, and no sound is produced. Similarly, if the cuff 16 of a manual sphygmomanometer 10 is placed around a patient's upper arm 12 and inflated to a pressure above the patient's systolic blood pressure 26, there will be no sound audible via a stethoscope 20 placed over the brachial artery 16. This is because the pressure in the cuff 16 is high enough such that it completely occludes the blood flow. This is similar to a flexible tube or pipe with fluid in it that is being pinched shut.

If the pressure is dropped to a level equal to that of the patient's systolic blood pressure 26, the first Korotkoff sound 32 in FIG. 10 will be heard. As the pressure in the cuff 16 is the same as the pressure produced by the heart, some blood will be able to pass through the upper arm 12 when the pressure in the artery 18 rises during systole. This blood flows in spurts as the pressure in the artery 18 rises above the pressure in the cuff 16 and then drops back down beyond the cuffed region, resulting in turbulence that produces an audible sound 32. As the pressure in the cuff 16 is allowed to fall further, thumping sounds continue to be heard as long as the pressure in the cuff 16 is between the systolic 26 and diastolic 30 pressures, as the arterial pressure keeps on rising above and dropping back below the pressure in the cuff 16. Eventually, as the pressure in the cuff 16 drops further, the sounds change in quality, then become muted, and finally disappear altogether. This occurs because, as the pressure in the cuff 16 drops below the diastolic blood pressure 30, the cuff 16 no longer provides any restriction to blood flow allowing the blood flow to become smooth again with no turbulence and thus produce no further audible sound.

There are five Korotkoff sounds that are described. The first Korotkoff sound 32 is the snapping sound first heard at the systolic pressure. Clear tapping, repetitive sounds for at least two consecutive beats is generally considered to occur at the systolic pressure 26. The second Korotkoff sounds 34 are the murmurs heard for most of the area between the systolic 26 and diastolic 30 pressures. The third Korotkoff sound 36 is described as a loud, crisp tapping sound. The fourth Korotkoff sound 38, at pressures within 10 mmHg above the diastolic blood pressure 30, was described as "thumping" and "muting". The fifth Korotkoff sound 40 is silence as the cuff 16 pressure drops below the diastolic blood pressure 30. The disappearance of sound is considered to occur at the diastolic blood pressure 30, actually about 2 mmHg below the last sound heard.

In addition to the Korotkoff sound heard through the stethoscope 20 in operation of a manual sphygmomanometer 10 the needle or gauge 28 of a manual sphygmomanometer 10 shows a slight "bump" as the blood rushes through the artery 18 causing a slightly elevated pressure reading. This visually noticeable bump in the pressure display occurs just before the first Korotkoff sound 32 and continues at pressures below the fifth Korotkoff sound 40. These visible gauge bumps are referenced herein as Korotkoff gauge bumps merely for the purpose of having a uniform reference for these features. Visualizing and recognizing the Korotkoff gauge bumps are also an important aspect of manual sphygmomanometer training.

Training

With the above described background it is important to have a method of accurately training medical professionals to accurately take blood pressure readings of patients using manual sphygmomanometer.

A number of blood pressure medical simulators have been developed to assist training medical professionals to accurately take blood pressure readings of patients using manual sphygmomanometer. For example see the LIFE/FORM® Blood pressure simulator using a manikin arm through which fluid is supplied at the desired pressure. Similarly Gaumard supplies a S415 BLOOD PRESSURE TRAINING SYSTEM™ which includes a full-size adult left arm that may also be attached to any Gaumard adult manikin and which is programmable to the desired simulated blood pressure. Laerdal also manufactures a BLOOD PRESSURE TRAINING ARM™ that provides "a lifelike, adult arm with an electronic trainer" designed for training the procedure of blood pressure measurement using a manual sphygmomanometer. Similarly, Armstrong Medical Industries manufactures a BLOOD PRESSURE SIMULATOR in the form of a manikin arm type device which is described as "a lifelike simulator" that "allows the presetting of values for both systolic and diastolic pressures. It provides an excellent means to practice listening to and distinguishing blood pressure sounds prior to actual clinical experience. It is possible to audibly discern the five Korotkoff phases. The electronically generated sounds are digitally recorded." While these simulators provide effective tools for supplying the trainees with a wide range of blood pressures to obtain and provide a method of verifying the accuracy of the trainee's results, they do not provide the real live aspects of interacting with a human regardless of how "lifelike" the systems become.

In recognizing the drawbacks of existing manikin based simulators educators will often have trainees work on trial subjects, most commonly by pairing the trainees together in which they switch from being the trainee and patient. This training has the advantage of introducing live subjects with all the aspects and nuances of interacting with live subjects that remains difficult to capture with manikin type simulators. However this training technique offers very little variation in the blood pressures that the trainees will experience (in general the class room subjects have an average blood pressure) and does not allow the teacher to easily verify the results of a particular trainee or to present a trainee with a desired blood pressure to measure.

Another medical training approach used in medical training is using live actors as patients who are reporting a selections of symptoms associated with a given malady or condition. In such training exercises the trainees are told to measure the actor/patient's blood pressure (which is often not indicative of an actor's simulated condition), and then told to ignore the results and assume that the trainee recorded results then given to the trainee and more in line with the actor's simulated condition. This live training technique also has the advantage of having trainees work with live subjects with all the aspects and nuances of interacting with live subjects, but it does not allow the trainee to actually obtain abnormal pressures (barring an actual abnormal condition of the actor) and lessens the realism of the training event as the trainee must disregard the obtained values and imagine some other imaginary set of values. This method also fails to allow the trainer to validate the accuracy of an abnormal blood pressure measurement obtained by the trainee.

There remains a need in the art to effectively expand the useful tools applicable to medical teachers and to provide effective tools for use with live subjects that supply the trainees of manual sphygmomanometer with a wide range of blood pressures to obtain and provide a system of verifying the accuracy of the trainee's results.

SUMMARY OF THE INVENTION

One aspect of the present invention provides a universal sphygmomanometer simulator for live training and evaluation. The term "universal" within the meaning of this application is intended to indicate that the simulator of the present invention can be used with any manikin brand for manikin based simulated patients and also with live simulated patients. The concept that the simulator is for "live training" indicates, within the meaning of this application, that the simulator is suitable for and can be used with living simulated patients (actors), and that the device will simulate the blood pressure readings (rather than merely display the actors actual blood pressure). The concept of using the simulator for evaluation within the meaning of this application means that the device provides a verifiable result whereby the trainee's performance can be objectively evaluated.

One aspect of the invention provides a Sphygmomanometer simulator for live training comprising: a cuff configured to be placed around an extremity of a simulated patient; a rigid walled pressure vessel within the cuff; an inflator coupled to the rigid walled vessel to selectively increase the pressure within the pressure vessel; a release valve for selectively releasing the pressure within the pressure vessel; a pressure sensor within the cuff measuring the pressure within the pressure vessel; a cuff controller within the cuff receiving the pressure sensor measurements of the pressure sensor; a speaker within the cuff controlled by the cuff controller and configured to emit designated simulated Korotkoff sounds associated with a simulated blood pressure for the simulated patient and associated with the pressure of the pressure vessel; a visual gauge controlled by the cuff controller and configured to display a pressure associated with the pressure in the pressure vessel; and a user controller coupled to the cuff controller for inputting the simulated blood pressure for the simulated patient.

One aspect of the present invention provides a sphygmomanometer simulator for live training comprising: a cuff configured to be placed by the medical professional trainee smoothly and snugly around an upper arm of a simulated patient (manikin or human); a rigid walled pressure vessel within the cuff; a manual inflator coupled to the rigid walled vessel to selectively increase the pressure within the pressure vessel; a manual release valve for selectively releasing the pressure within the pressure vessel; a pressure sensor within the cuff measuring the pressure within the pressure vessel; a cuff controller within the cuff receiving the pressure sensor measurements of the pressure sensor; a speaker within the cuff controlled by the cuff controller and configured to emit designated simulated Korotkoff sounds associated with a simulated blood pressure for the simulated patient and associated with the pressure of the pressure vessel; a visual gauge controlled by the cuff controller and configured to display a desired pressure associated with the pressure in the pressure vessel and simulated Korotkoff gauge bumps associated with the simulated blood pressure for the simulated patient; and a user controller coupled to the cuff controller for inputting the simulated blood pressure for the simulated patient.

These and other advantages of the present invention will be clarified in the brief description of the preferred embodiment taken together with the drawings in which like reference numerals represent like elements throughout.

DESCRIPTION OF THE PREFERRED EMBODIMENTS

Figure 1A:
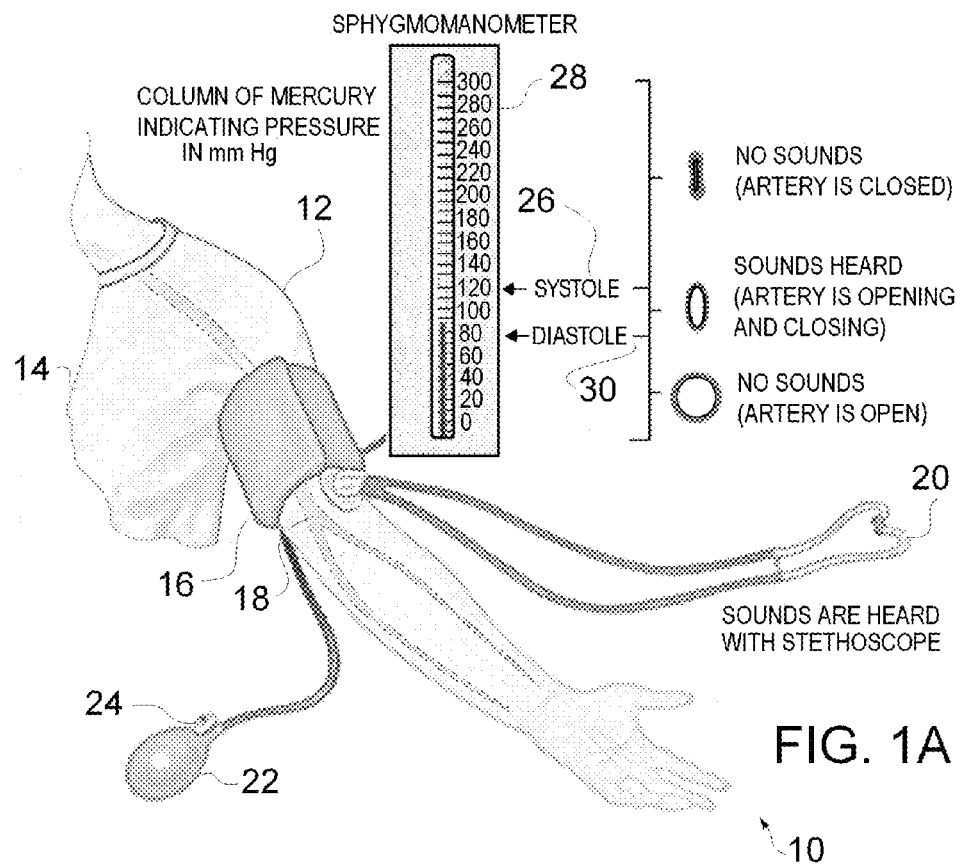
FIG. 1A is a figure illustrating the operation of a conventional manual sphygmomanometer.
Figure 1C:
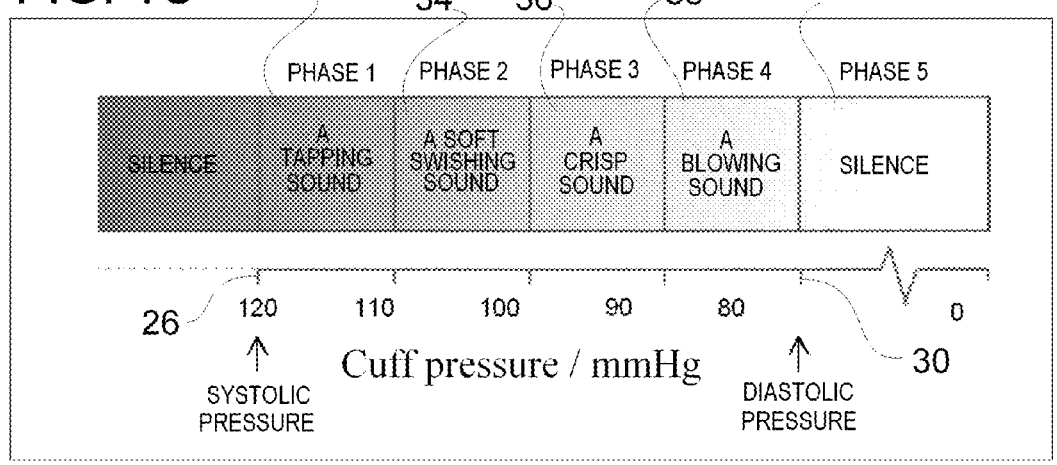
FIG. 1C is a chart illustrating the pressure aspects and Korotkoff sounds associated with the operation of a conventional manual sphygmomanometer.
Figure 2:
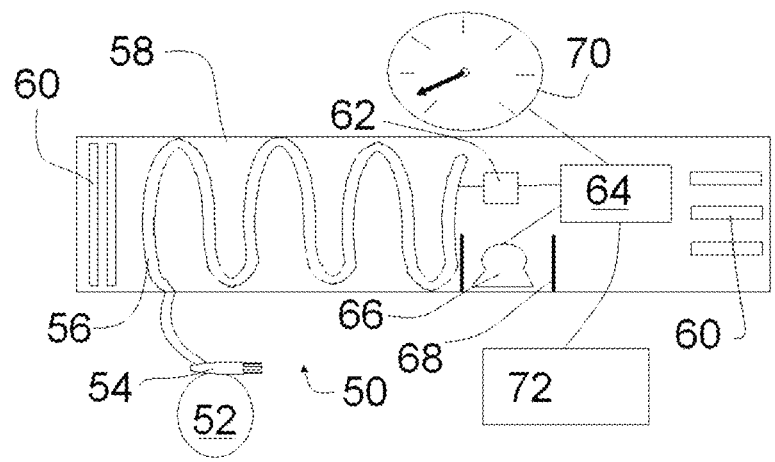
FIG. 2 is a schematic illustration of a universal sphygmomanometer simulator for live training and evaluation formed according to one aspect of the present invention.
Figure 1B:
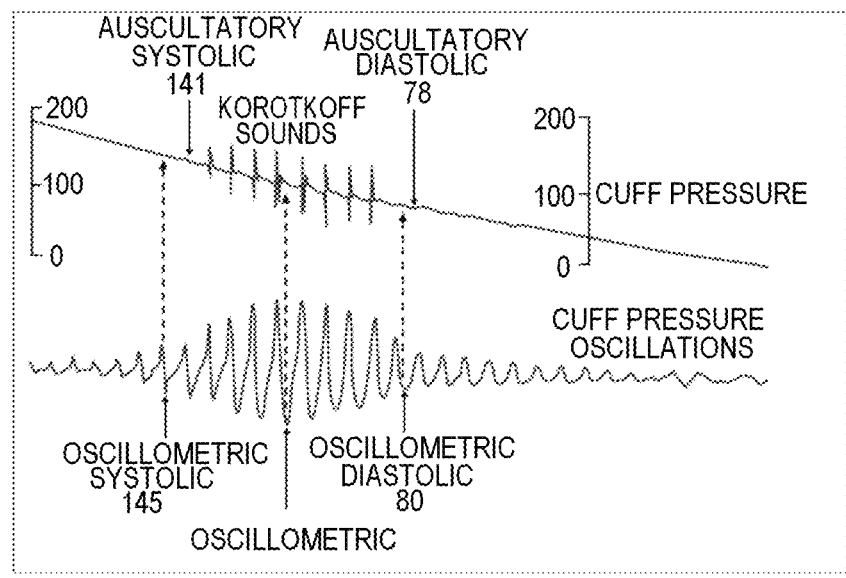
FIG. 1B is a chart of the pressure and sounds associated with the operation of a conventional manual sphygmomanometer.
Figure 3:
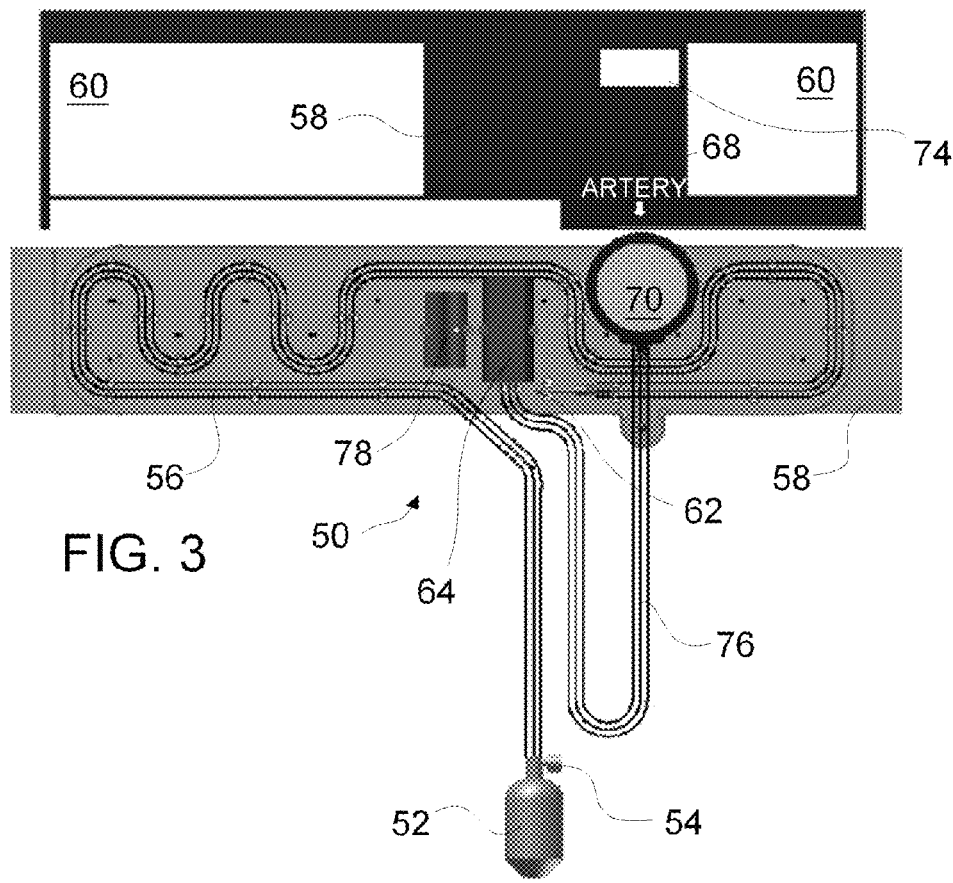
FIG. 3 is another schematic illustration of a universal sphygmomanometer simulator for live training and evaluation formed according to one aspect of the present invention.
Figure 4A:
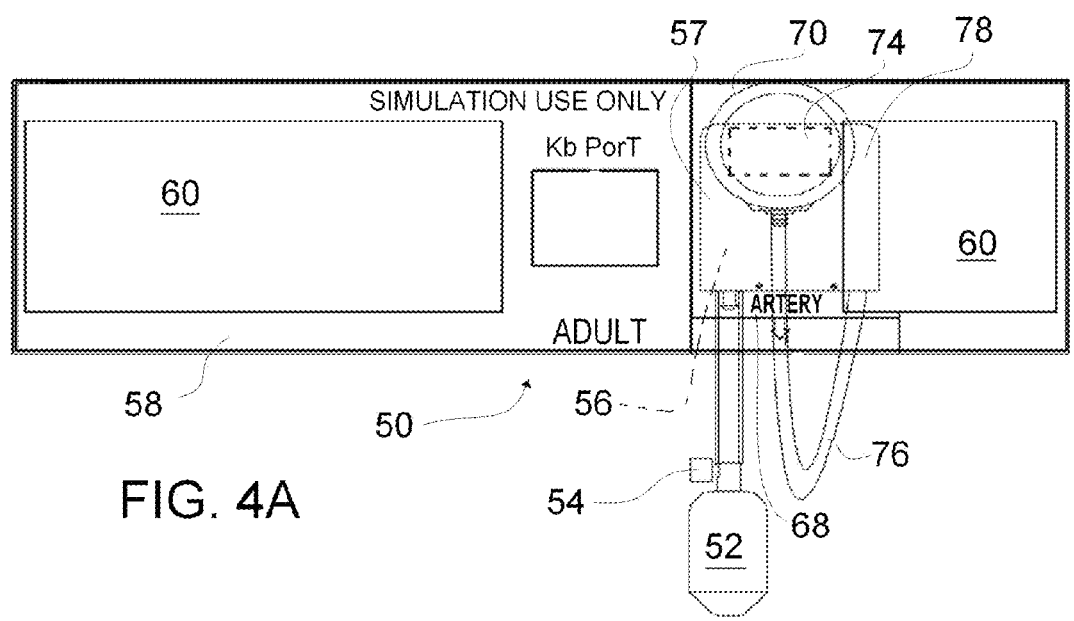
FIG. 4A is another schematic illustration of a universal sphygmomanometer simulator for live training and evaluation formed according to one aspect of the present invention.
Figure 4B:
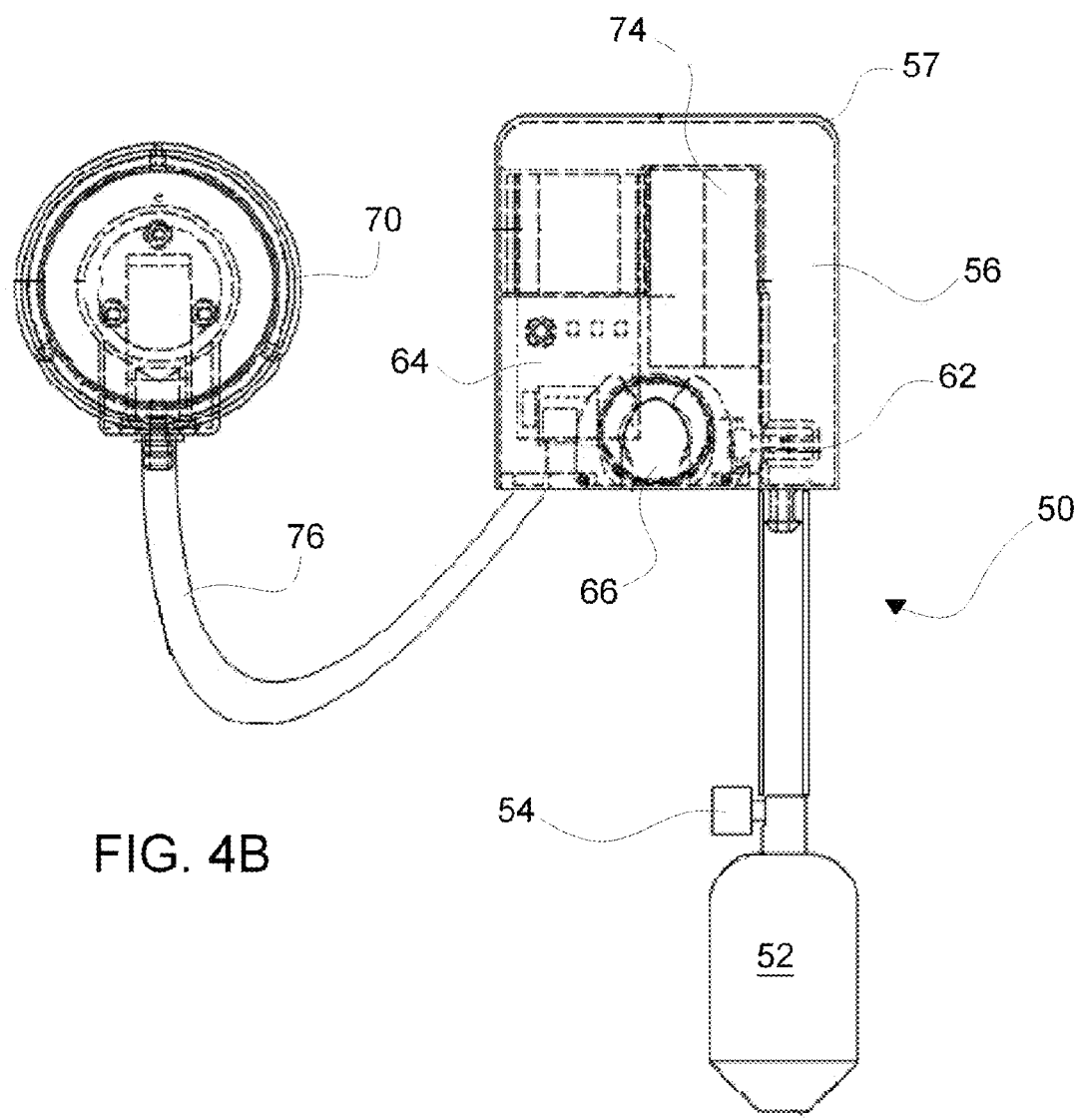
FIG. 4B is a schematic illustration of the universal sphygmomanometer simulator for live training and evaluation of FIG. 4A with the cuff removed for clarity.

FIGS. 2, 3 and 4A are schematic illustrations of a universal sphygmomanometer simulator 50 for live training and evaluation formed according to one aspect of the present invention. FIG. 3 is an exploded view of the sphygmomanometer simulator 50 showing the exterior of the cuff 58 above the inner cuff 58. While most aspects of the invention are clear in both figures, some aspects are better illustrated in FIG. 2 while others are better illustrated in the FIG. 3. FIG. 4A is another schematic illustration of a universal sphygmomanometer simulator 50 for live training and evaluation formed according to one aspect of the present invention which can be better described after the embodiments of FIGS. 2 and 3. FIG. 4B is a schematic illustration of the universal sphygmomanometer simulator 50 for live training and evaluation of FIG. 4A with the cuff removed for clarity.

As discussed above and further elaborated herein the term universal is intended to indicate that the simulator 50 of the present invention can be used with any manikin brand for manikin based simulated patients and with live simulated patients. The concept that the simulator 50 is for live training indicates that the simulator 50 is suitable for and can be used with living simulated patients (actors), and that the simulator 50 will simulate the blood pressure readings (rather than merely display the actors actual blood pressure). The concept of using the simulator 50 for evaluation means that the simulator 50 provides a verifiable result whereby the trainee's performance can be objectively evaluated.

The sphygmomanometer simulator 50 for live training includes a manual inflator 52 and a manual release valve 54 that are substantially identical to the bulb 22 and valve 24 of the manual sphygmomanometer discussed above. In fact it is preferred if the manual inflator 52 and a manual release valve 54 have the same look and feel of conventional bulbs 22 and valves 24 of existing manual sphygmomanometers 10 so that trainees become accustomed to the conventional bulbs 22 and valves 24 of existing manual sphygmomanometers 10. It is particularly helpful as a training aid that the sphygmomanometer simulator 50 is substantially indistinguishable to the trainee from a manual sphygmomanometer 10.

The sphygmomanometer simulator 50 includes a substantially conventional cuff 58 configured to be placed by the medical professional trainee smoothly and snugly around an upper arm of a simulated patient, such as by using VELCO® hook and loop type fasteners 60. The cuff 58 is preferably substantially identical in appearance and in operation to the trainee as the cuff 16 of the manual sphygmomanometer 10. The cuff 58 can be formed in various sizes (adults, children, or for thighs) as with cuffs 16 of manual sphygmomanometers 10. The simulated blood pressure cuff 58 is generally formed to go onto the upper arm at heart level, as is the most common position for manual sphygmomanometers 10. It should be stated that the sphygmomanometer simulator 50 can be used on any artery that can be occluded such as the wrist or leg. There are existing manual sphygmomanometers 10 with cuff sized for these applications, and it is contemplated that the present invention may provide the sphygmomanometer simulator 50 with a cuff 58 designed to be used in other parts of the body as well for proper training of these alternative manual sphygmomanometers 10. The remaining portions of this specification will still discuss the upper arm placement as that is the most common, which discussion is merely for clarification and illustration of the invention.

The sphygmomanometer simulator 50 includes a rigid walled pressure vessel 56, or bladder, within the cuff 58 and coupled to the manual inflator 52 and the manual release valve 54. The rigid walled pressure vessel 56 differs from the expanding bladder of a manual sphygmomanometer 10 in a significant respect, in that as the pressure is increased in the vessel 56 the patient's artery 18 is not occluded because the vessel 56 has substantially rigid walls which isolate the pressure increase from the arm of the patient. In the embodiment of FIGS. 4A and B the rigid walls forming the pressure vessel 56 also form a housing 57 for a number of the remaining components of the simulator 50.

The vessel 56 can be formed as an extended coiled length of rigid walled plastic tubing or as a chamber in housing 57. The volume of the pressure vessel 56 is selected to be sufficiently long such that tactile feedback to the cuff 58 closely mimics the tactile feedback of bulb 22 of a manual sphygmomanometer 10 in conventional pressure ranges. Mimicking this tactile response will enhance the training aspect of the sphygmomanometer simulator 50. Suitable tubing types and lengths include a total air volume which generally should be greater than or equal to about 50 CC to achieve a realistic feel. For example if a tube with a 6.35 mm inner wall diameter is used then it needs to be at least 1.5 meters long. The longer the tube the more realistic the feel of the sphygmomanometer simulator 50 to the trainee. The total length of the hose is limited by factors such as bend radius pressure cuff size and tube outer diameter. The pressure vessel 56 can take a form other than coiled tubing as the chamber in housing 57 or such as simply a bladder with a ridged wall. Further it is possible to use non-ridged walled structures for the vessel 56 as long as there is included another mechanism to isolate the pressure in this modified vessel from the subjects arm to prevent occlusion of the artery 18. For example a ridged backing in the cuff 58 preventing the constriction of the cuff 58 by the expansion of a flexible walled vessel 56, could be used as an equivalent of the rigid walled vessel 56, provided that such ridged backing in cuff 58 does not alter the realistic look and feel of the cuff 58 (as compared with cuff 16 of a manual sphygmomanometer 10). FIG. 3 illustrates a semi-ridged backing forming the lower cuff 58 to which the tubing forming vessel 56 is mounted together with the battery 78 and controller 64. Returning to the structure of the vessel 56, having the rigid vessel 56 formed of coiled tubing as shown appears to be an easy method of accomplishing the requirements for the simulator 50. As for FIGS. 4A and B forming the vessel 56 as a chamber within housing 57 allows the unit formed by the housing 57 to be easily coupled to cuffs 58 of different sizes.

The sphygmomanometer simulator 50 includes a pressure sensor 62, such as a conventional pressure transducer, within the cuff 58 measuring the pressure within the pressure vessel 56. The pressure sensor may be at the end of a reducing connector, as shown in FIG. 3, at the end of the tubing forming the vessel 56. The sphygmomanometer simulator 50 includes a cuff controller 64 within the cuff 58 receiving the pressure sensor measurements of the pressure sensor 62.

The sphygmomanometer simulator 50 includes a speaker 66 within the cuff 58 which is controlled by the cuff controller 64. The speaker 66, as described in greater detail below, is configured to emit designated simulated Korotkoff sounds associated with a simulated blood pressure for the simulated patient and associated with the pressure of the pressure vessel 56.

The cuff 58 may include visual indicia 68 that indicate to the trainee the position or the general appropriate range for placement of the stethoscope 20 over the brachial artery 18. The use of indicia 68 is known for some cuffs 16 of manual sphygmomanometer 10 and is helpful in the sphygmomanometer simulator 50 as it allows the speaker 66 to be in close proximity to the stethoscope 20 of the trainee, assuming the trainee properly places the cuff 58 and then the stethoscope 20 in accordance with indicia 68. The proximity of the speaker 66 to the indicia 68 is believed to provide some positive training feedback to the trainee during operation of the simulator 50, as the sounds will become clearer the more accurately positioned that the trainee places the stethoscope 20.

The sphygmomanometer simulator 50 includes a visual gauge 70 controlled by the cuff controller 64 and configured to display a pressure associated with the pressure in the pressure vessel 56 and simulated Korotkoff gauge bumps associated with the simulated blood pressure for the simulated patient as will be discussed in detail below. The pressure shown on gauge 70 need not be a direct correlation to the pressure sensed by sensor 62 but will be some translational function thereof as determined by the controller 64. The gauge 70 may be easily formed as an analog dial or as a digital number display which is controlled by the cuff controller 64. The gauge 70 may be held in place with a strap 74 on the exterior of the cuff 58 as shown in FIG. 3, which is analogous to some common cuffs of existing manual sphygmomanometers 10. The coupling 76, shown best in FIG. 3, between the controller 64 and the gauge 70 may be formed as electrical wire coupling housed in a tubing to mimic the pneumatic coupling found in manual sphygmomanometers 10. The sphygmomanometer simulator 50 includes a battery power source 78 to supply power for operation and may have an on/off switch and recharging port or battery replacement access, as needed.

The figures show a portable simulator 50, however the simulator 50 may be a wall mounted unit in which the display 70 is mounted to the wall.

The main difference between the embodiments of FIGS. 2 and 3 and that of FIGS. 4A and B is that figures A and B consolidate the majority of the components into a housing 57 including the chamber 56. This allows the unit to be easily added to cuffs 58 by merely adding a pocket for the housing 57 in the cuff 58.

The sphygmomanometer simulator 50 includes a user controller 72, such as a laptop, tablet computer, smartphone, PDA, or the like, coupled to the cuff controller 64 for, at least, inputting the simulated blood pressure for the simulated patient. The coupling may be a wireless connection or a wired connection and may be severed after the scenario is uploaded to the cuff controller 64. The uploading may include a transfer of the desired simulated blood pressure reading for an event together with desired simulated Korotkoff sounds associated with a simulated blood pressure for the simulated patient and the simulated Korotkoff gauge bumps associated with the simulated blood pressure for the simulated patient.

In operation the trainer will utilize the user controller 72 to input or transfer the desired simulated blood pressure reading for an event together with desired simulated Korotkoff sounds associated with a simulated blood pressure for the simulated patient and the simulated Korotkoff gauge bumps associated with the simulated blood pressure for the simulated patient. As discussed the controller 72 may be removed before giving the simulator 50 to the trainee. Now the cuff 58 of the sphygmomanometer simulator 50 is placed by the medical professional trainee smoothly and snugly around an upper arm 12 of a patient 14, at roughly the same vertical height as the heart while the patient is seated with the arm 12 supported.

In a manual sphygmomanometer 10 the cuff 16 would now be inflated via bulb 22 until the artery 18 is completely occluded. Here with the sphygmomanometer simulator 50, the trainee will increase the pressure in the pressure vessel 56 to a point above the designated simulated blood pressure such that the artery would otherwise be occluded. As an aside, should the trainee fail to exceed the upper boundary of the designated simulated blood pressure the controller 64 will send appropriate simulated Korotkoff sounds to speaker 66 and appropriate simulated Korotkoff gauge bumps to the display 70 such that the trainee will receive the same auditory and visual response as would be expected with a manual sphygmomanometer 10.

With the cuff 58 thus inflated until the artery 18 is theoretically completely occluded, a stethoscope 20 is placed in a position to listen to sounds (Korotkoff sounds) through the brachial artery 18. The indicia 68 will guide the trainee with the placement of the stethoscope 20 and such proper placement will be in close proximity to the speaker 66 (which is within the cuff and not visible to the trainee. It is important to note that the rigid tubing or rigid backing or chamber forming vessel 56 prevents the occlusion of the artery 18 in the simulated patient, who may be a live patient, and thus prevents any of the patients actual Korotkoff sounds from interfering with the operation of the simulator 50 as the live patient will be exhibiting the fifth Korotkoff sound (silence).

The medical professional trainee slowly releases the pressure in the pressure vessel 56 via releasing manual valve 54. As the pressure in the pressure vessel 56 falls, a "whooshing" or pounding sound is generated (the first simulated Korotkoff sound) and passed through the speaker 66. The controller 64 uses the pressure signal from sensor 62 and the designated simulated blood pressure to send the first simulated Korotkoff sound at the appropriate pressure, namely that pressure when blood flow would first starts again in the artery 18 had the simulator 50 been a manual sphygmomanometer 10 blocking the artery 18 and the patient has the designated blood pressure. The pressure, shown on display or gauge 70, at which this first simulated Korotkoff sound began is (hopefully) noted by the trainee and recorded as the systolic blood pressure 26.

The pressure vessel 56 pressure is further released until the simulated Korotkoff sounds can no longer be heard. The simulated Korotkoff sounds heard through speaker 66 and the generally adjacent stethoscope 20 are controlled throughout by the controller 64 in association with the designated simulated blood pressure and the measured pressure of the vessel 56. The pressure reading on display 70 when the simulated Korotkoff sounds (the fourth simulated Korotkoff sound) can no longer be heard is recorded by the trainee (hopefully) as the diastolic blood pressure 30.

There are four audible simulated Korotkoff sounds that are associated with a given simulated blood pressure as the fifth simulated Korotkoff sound is silence. These simulated Korotkoff sounds naturally match the actual Korotkoff sounds that would be expected t be produced, and the first Korotkoff sound 32 is the snapping sound first heard at the systolic pressure. As noted above, clear tapping, repetitive sounds for at least two consecutive beats is generally considered to occur at the systolic pressure 26. The second Korotkoff sounds 34 are the murmurs heard for most of the area between the systolic 26 and diastolic 30 pressures. The third Korotkoff sound 36 is described as a loud, crisp tapping sound. The fourth Korotkoff sound 38, generally at pressures within 10 mmHg above the diastolic blood pressure 30, was described as "thumping" and "muting". The fifth Korotkoff sound 40 is silence (as the cuff 16 pressure of a manual sphygmomanometer 10 drops below the diastolic blood pressure 30). The disappearance of sound is considered to occur at the diastolic blood pressure 30, actually about 2 mmHg below the last sound heard. The fact that the fifth Korotkoff sound is silence allows the simulator 50 to effectively operate on live patients and on existing blood pressure manikins as well as a mere manikin arm, making the simulator 50 of the present invention truly universal.

In addition to the simulated Korotkoff sounds heard via speaker 66 through the stethoscope 20, in operation of the sphygmomanometer simulator 50 the needle or gauge 70 is controlled to shows a slight simulated Korotkoff gauge bumps. As with the simulated Korotkoff sounds the simulated Korotkoff gauge bumps are incorporated into the pressure display 70 at pressure values determined by the simulated blood pressure of the simulated patient.

The controller 64 may include a randomizing function to modify the simulated Korotkoff gauge bumps to be slightly different within acceptable ranges such that the exact same display characteristics is not shown from event to event to add more realism. In a similar fashion, the simulated Korotkoff sounds may have noise or other variability added within acceptable ranges to create some audible uniqueness with each trial to better approximate a manual sphygmomanometer.

The sphygmomanometer simulator 50 is universal as it can be used with any manikin brand for manikin based simulated patients (whether they have a blood pressure simulator or not) and with live simulated patients. The sphygmomanometer simulator 50 is well suited for live training with living simulated patients (actors) as it will simulate the blood pressure readings rather than merely display the actor's actual blood pressure. The sphygmomanometer simulator 50 is effective for evaluation as it provides a verifiable result whereby the trainee's performance can be objectively evaluated.

Other alternatives of the simulator 50 are contemplated such as an "all electronic" version in which the pressure vessel 56 is removed and the sensor 62 obtains the designated pressure directly from a simulated bulb (simulated because it is not actually pumping pressure. Here the valve 54 would be simulated as it is not used to release any pressure, however the simulated bulb would need the tactile and audible feedback necessary to mimic conventional operation.

Although the present invention has been described with particularity herein, the scope of the present invention is not limited to the specific embodiment disclosed. It will be apparent to those of ordinary skill in the art that various modifications may be made to the present invention without departing from the spirit and scope thereof.

What is claimed is:

1. A sphygmomanometer simulator for live training and evaluation, comprising:
    a cuff configured to be placed around an extremity of a manikin based simulated patient and a live based simulated patient,
    wherein the cuff is structured to avoid generation of actual Korotkoff sounds from a live patient when placed around an extremity of the live patient even after the cuff is inflated, and
    wherein the cuff comprises a rigid walled pressure vessel provided within the cuff and structured to prevent occlusion of an artery when the cuff is placed around an extremity of the live patient and the cuff is inflated,
    an inflator coupled to the rigid walled pressure vessel to selectively increase a pressure within the rigid walled pressure vessel, and
    a release valve coupled to the rigid walled pressure vessel for selectively releasing the pressure within the rigid walled pressure vessel.

2. The sphygmomanometer simulator for live training and evaluation according to claim 1 further including a pressure sensor within the cuff measuring the pressure within the pressure vessel and a cuff controller within the cuff receiving the pressure sensor measurements of the pressure sensor.

3. The sphygmomanometer simulator for live training and evaluation according to claim 2 further including a speaker within the cuff controlled by the cuff controller and configured to emit designated simulated Korotkoff sounds associated with a simulated blood pressure for the manikin or live based simulated patient and associated with the pressure of the pressure vessel.

4. The sphygmomanometer simulator for live training and evaluation according to claim 3 further including a visual gauge controlled by the cuff controller and configured to display a pressure associated with the pressure in the pressure vessel.

5. The sphygmomanometer simulator for live training and evaluation according to claim 4 further including a user controller coupled to the cuff controller for inputting the simulated blood pressure for the manikin or live based simulated patient.

6. The sphygmomanometer simulator for live training and evaluation according to claim 4 wherein the display is configured to display simulated Korotkoff gauge bumps associated with the simulated blood pressure for the manikin or live based simulated patient.

7. The sphygmomanometer simulator for live training and evaluation according to claim 4 wherein the inflator is a manual inflator.

8. The sphygmomanometer simulator for live training and evaluation according to claim 4 wherein the release valve is a manual release valve.

9. The sphygmomanometer simulator for live training and evaluation according to claim 4 wherein the cuff is configured to be placed by a medical professional trainee smoothly and snugly around an upper arm of the manikin or live based simulated patient.

10. The sphygmomanometer simulator for live training and evaluation according to claim 4 further including a user controller coupled to the cuff controller for inputting the simulated blood pressure for the manikin or live based simulated patient and wherein the user controller is wirelessly coupled to the cuff controller.

11. A sphygmomanometer simulator for live training comprising:
    a cuff configured to be placed around an extremity of a manikin based simulated patient and a live based simulated patient;
    a rigid walled pressure vessel within the cuff and structured to prevent occlusion of an artery and avoid generation of actual Korotkoff sounds when the cuff is placed around an extremity of a live patient and the cuff is inflated;
    an inflator coupled to the rigid walled vessel to selectively increase the pressure within the pressure vessel;
    a release valve coupled to the rigid walled vessel for selectively releasing the pressure within the pressure vessel;
    a pressure sensor within the cuff measuring the pressure within the pressure vessel;
    a cuff controller within the cuff receiving the pressure sensor measurements of the pressure sensor;
    a speaker within the cuff controlled by the cuff controller and configured to emit designated simulated Korotkoff sounds associated with a simulated blood pressure for the manikin or live based simulated patient and associated with the pressure of the pressure vessel;
    a visual gauge controlled by the cuff controller and configured to display a pressure associated with the pressure in the pressure vessel; and
    a user controller coupled to the cuff controller for inputting the simulated blood pressure for the manikin or live based simulated patient.

12. The sphygmomanometer simulator for live training according to claim 11 wherein the display is configured to display simulated Korotkoff gauge bumps associated with the simulated blood pressure for the manikin or live based simulated patient.

13. The sphygmomanometer simulator for live training according to claim 12 wherein the inflator is a manual inflator.

14. The sphygmomanometer simulator for live training according to claim 13 wherein the release valve is a manual release valve.

15. The sphygmomanometer simulator for live training according to claim 14 wherein the cuff is configured to be placed by a medical professional trainee smoothly and snugly around an upper arm of the manikin or live based simulated patient.

16. The sphygmomanometer simulator for live training according to claim 15 wherein the user controller is wirelessly coupled to the cuff controller.

17. The sphygmomanometer simulator for live training according to claim 12 wherein the cuff is configured to be placed by a medical professional trainee smoothly and snugly around an upper arm of the manikin or live based simulated patient, and wherein the user controller is wirelessly coupled to the cuff controller.

18. A sphygmomanometer simulator for live training comprising:
- a cuff configured to be placed by a medical professional trainee smoothly and snugly around an upper arm or other designated position of a manikin based simulated patient and a live based simulated patient;
- a rigid walled pressure vessel within the cuff and structured to prevent occlusion of an artery and avoid generation of actual Korotkoff sounds when the cuff is placed around an extremity of a live patient and the cuff is inflated;
- a manual inflator coupled to the rigid walled vessel to selectively increase the pressure within the pressure vessel;
- a manual valve coupled to the rigid walled vessel for selectively releasing the pressure within the pressure vessel;
- a pressure sensor within the cuff measuring the pressure within the pressure vessel;
- a cuff controller within the cuff receiving the pressure sensor measurements of the pressure sensor;
- a speaker within the cuff controlled by the cuff controller and configured to emit designated simulated Korotkoff sounds associated with a simulated blood pressure for the manikin or live based simulated patient and associated with the pressure of the pressure vessel;
- a visual gauge controlled by the cuff controller and configured to display a pressure associated with the pressure in the pressure vessel and simulated Korotkoff gauge bumps associated with the simulated blood pressure for the manikin or live based simulated patient; and
- a user controller coupled to the cuff controller for inputting the simulated blood pressure for the manikin or live based simulated patient.

19. The sphygmomanometer simulator for live training according to claim 1, wherein the rigid walled pressure vessel comprises an extended length of coiled tubing.

20. The sphygmomanometer simulator for live training according to claim 11, wherein the rigid walled pressure vessel comprises an extended length of coiled tubing.

21. The sphygmomanometer simulator for live training according to claim 18, wherein the rigid walled pressure vessel comprises an extended length of coiled tubing.

* * * * *